US008076484B2

(12) United States Patent
Hsu

(10) Patent No.: US 8,076,484 B2
(45) Date of Patent: Dec. 13, 2011

(54) MODIFIED GREEN TEA POLYPHENOL FORMULATIONS

(75) Inventor: Stephen D. Hsu, Evans, GA (US)

(73) Assignee: Georgia Health Science University Research Institute, Inc., Augusta, GA (US)

( * ) Notice: Subject to any disclaimer, the term of this patent is extended or adjusted under 35 U.S.C. 154(b) by 895 days.

(21) Appl. No.: 12/063,139

(22) PCT Filed: Aug. 10, 2006

(86) PCT No.: PCT/US2006/031120

§ 371 (c)(1),
(2), (4) Date: Feb. 7, 2008

(87) PCT Pub. No.: WO2007/021789

PCT Pub. Date: Feb. 22, 2007

(65) Prior Publication Data

US 2008/0176956 A1 Jul. 24, 2008

Related U.S. Application Data

(60) Provisional application No. 60/707,234, filed on Aug. 11, 2005.

(51) Int. Cl.
*C07D 215/38* (2006.01)
(52) U.S. Cl. ..................................... 546/159
(58) Field of Classification Search .................. 546/159
See application file for complete search history.

(56) References Cited

U.S. PATENT DOCUMENTS

| | | | |
|---|---|---|---|
| 5,073,372 | A | 12/1991 | Turner et al. |
| 5,087,445 | A | 2/1992 | Haffey et al. |
| 5,160,731 | A | 11/1992 | Sabatelli et al. |
| 6,410,052 | B1 | 6/2002 | Morre et al. |
| 6,428,818 | B1 | 8/2002 | Morre et al. |
| 6,713,506 | B2 | 3/2004 | Dou et al. |
| 7,358,383 | B2 | 4/2008 | Dou et al. |
| 2004/0186167 | A1 | 9/2004 | Dou et al. |
| 2004/0191842 | A1 | 9/2004 | Hsu et al. |

FOREIGN PATENT DOCUMENTS

| | | | |
|---|---|---|---|
| CN | 1197786 A | | 11/1998 |
| CN | 1067675 C | | 6/2001 |
| CN | 1448395 | * | 10/2003 |
| WO | WO 2004052873 | | 6/2004 |

OTHER PUBLICATIONS

Yoshino, J Agric Food Chem, vol. 52, pp. 4660-4663, 2004.*
Chen, CA 142:423180 abstract only of Chaye Kexue, 2003, vol. 23(2), pp. 115-118.*
Chen, CA 142:37216, abstract only of Zhongguo Liangyou Zuebao, vol. 18(5), pp. 77-79, 2003.*
Chen, CA 138:299947 abstract only of J of Chrom A, vol. 982(1), pp. 163-165, 2002.*
Ivanova, CA 140:300406, abstract only of Khimiya Rastitel'nogo Syr'ya, vol. (4), pp. 5-13, 2002.*
Adhami, et al., "Molecular targets for green tea in prostate cancer prevention", *J. Nutr.*, 133:2417S-2424S (2003).
Ahmad, et al., "Identification and characterization of murine caspase-14, a new member of the caspase family", *Cancer Res.*, 58:5201-5205 (1998).
Ahmed, et al., "Green tea polyphenol epigallocatechin-3-gallate (EGCG) differentially inhibits interleukin-1 beta-induced expression of matrix metalloproteinase-1 and—13 in human chondrocytes", *J. Pharmacol. Exp. Ther.*, 308(2):767-73(2004).
Alibardi, et al., "Ultrastructural localization of caspase-14 in human epidermis", *J. Histochem. Cytochem.*, 52(12):1561-74 (2004).
Asgharnejad, "Improving Oral Drug Transport via Prodrugs", in *Transport Processes in Pharmaceutical Systems*, (Amidon, et al., ed.), pp. 185-218, Marcell Dekker:New York, NY (2000).
Balant, et al., "Prodrugs for the improvement of drug absorption via different routes of administration", *Eur. J. Drug. Metab. Pharmacokinet*, 15(21:143-53 (1990).
Balasubramanian, et al., "Green tea polyphenol stimulates a Ras, MEKK1, MEK3, and p38 cascade to increase activator protein 1 factor-dependent involucrin gene expression in normal human keratinocytes", *J. Biol. Chem.*, 277:1828-1836 (2002).
Balimane and Sinko, "Involvement of multiple transporters in the oral absorption of nucleoside analogues", *Adv. Drug Delivery Rev.*, 39(1-3):183.209(1999).
Bikle, et al., "Calcium- and vitamin D-regulated keratinocyte differentiation", *Mol. Cell. Endocrinol.*, 177:161-171 (2001).
Bollag and Bollag, "1,25-Dihydroxyvitamin D(3), phospholipase D and protein kinase C in keratinocyte differentiation", *Mol. Cell. Endocrinol.*, 177:173-182 (2001).
Borke, et al., "Monoclonal antibodies to human erythrocyte membrane Ca +-Mg + + adenosine triphosphatase pump recognize an epitope in the basolateral membrane of human kidney distal tubule cell", *J. Clin. Invest.*, 80: 1225-1231 (1987).
Browne, "Fosphenytoin (Cerebyx)", *Clin. Neuropharmacol.*, 20(1):1-12 (1997).
Bundgaard, "Bioreversible derivatization of drugs—principle and applicability to improve the therapeutic effects of drugs", *Arch. Pharm. Chemi.*, 86(1):1-39 (1979). (with English abstract).
Cabrera, et al., "Beneficial effects of green tea—a review", *J. Am. Coll. Nutr.*, 25(2):79-99 (2006).
Chen & Du, "Isolation and purification of a novel long-chain acyl catechin from lipophilic tea polyphenols", *Chinese J. Chem.*, 21(7):979-981 (2003).
Chen, et al., "Degradation of green tea catechins in tea drinks", *J. Agric. Food Chem.*, 49(1):477-82 (2001).
Chen, et al., "Preparation, structure, and antioxidant activity of EGCG palmitate", *J. Zhejiang Univ.*, 30(4):422-425 (2003). (with English abstract).
Chen, et al., "Purification of long-chain fatty acid ester of epigallocatechin-3-0-gallate by high-speed counter-current chromatography", *J. Chromatogr.*, 982:163-165 (2002).
Chen, et al., "The main active component of lipophilic tea polyphenols and in vitro inhibition activity on ovarian cancer cells H0-8910", *J. Tea Sci.*, 23(2) 115-118 (2003). (with English abstract).

(Continued)

*Primary Examiner* — D M Seaman
(74) *Attorney, Agent, or Firm* — Pabst Patent Group LLP

(57) ABSTRACT

Modified green tea polyphenols and methods of their use are provided. One aspect provides compounds and compositions containing green tea polyphenols with one on more ester-linked fatty acids.

8 Claims, No Drawings

OTHER PUBLICATIONS

Chung, et al., "Dual mechanisms of green tea extract (EGCG)-induced cell survival in human epidermal keratinocytes", *FASEB J.*, 17(13):1913-5 (2003).

Dong, et al., "UVA light-induced DNA cleavage by isomeric methylbenz[a]anthracenes", *Chem. Res. Toxicol.*, 15(3):400-7 (2002).

Eckhart, et al., "Caspase-14: analysis of gene structure and mRNA expression during keratinocyte differentiation", *Biochem. Biophys. Res. Commun.*, 277:655-659 (2000).

Eckhart, et al., "Terminal differentiation of human keratinocytes and stratum corneum formation is associated with caspase-14 activation", *J. Invest. Dermatol.*, 115:1148-51 (2000).

Ege, "Reaction of Carboxylic Acids and Acid Derivatives with Alchohols as Neucleophiles. Acylation at Oxygen", in *Organic Chemistry: Structure and Reactivity*, 4$^{th}$Ed., pp. 573, Houghton Mifflin Company: New York, NY (1999).

Farquhar, et al., "Biologically reversible phosphate-protective groups", *J. Pharm. Sci.*, 72(3):324-325 (1983).

Fischer, et al., "Stratum corneum-derived caspase-14 is catalytically active", *FEBS Lett.*, 577(3):446.50, 2004.

Fleisher, et al., "Design of prodrugs for improved gastrointestinal absorption by intestinal enzyme targeting", *Methods Enzymol.*, 112:360-81 (1985).

Fleisher, et al., "Improved oral drug delivery: solubility limitations overcome by the use of prodrugs", *Adv. Drug Delivery Rev.*, 19(2): 115-130 (1996).

Gaspano, "The role of PUVA in the treatment of psoriasis. Photobiology issues related to skin-cancer incidence", *Am. J. Clin. Dermatol.*, 1:337-48 (2000).

Gillespie, et al., "Effects of oral consumption of the green tea polyphenol EGCG in a murine model for human Sjogren's syndrome, an autoimmune disease", *Life Sci.*, 83(17-18):581-8 (2008).

Han and Amidon, "Targeted prodrug design to optimize drug delivery", *AAPS Pharmsci.*, 2(1):E6 (2000).

Herbst, "Drug Latentiation", in *Progress in Drug Research*, (Jucker, ed.) 4:221-294, Birkhauser Verlag: Basel, Switzerland (1962).

Hiipakka, et al., "Structure-activity relationships for inhibition of human 5alpha-reductases by polyphenols", *Biochem. Pharmacol.*, 63(6):1165-1176 (2002).

Hsu and Dickinson, "A new approach to managing oral manifestations of Sjogren's syndrome and skin manifestations of lupus", *J. Biochem. Mol. Biol.*, 39(3):229-39 (2006).

Hsu, "Green tea and the skin", *J. Am. Acad. Dermatol.*, 52(6):1049-59 (2005).

Hsu, et al, "Induction of p57 is required for cell survival when exposed to green tea polyphenols",*Anticancer Research.*, 22:4115-4120 (2002).

Hsu, et al., "A mechanism-based in vitro anticancer drug screening approach for phenolic phytochemicals", *Assay Drug Dev. Technol.*, 1(5):611-8 (2003).

Hsu, et al., "Chemoprevention of oral cancer by green tea", *Gen. Dent.*, 50:140-6 (2002).

Hsu, et al., "Chemopreventive effects of green tea polyphenols correlate with reversible induction of p57 expression", *Anticancer Research*, 21:3743-3748 (2001).

Hsu, et al., "Green tea polypbenol-induced epithelial cell terminal differentiation is associated with coordinated expression of p57IKIP2 and caspase 14", *J. Pharmacol Exp. Ther.*, 312(3):884-90 (2005).

Hsu, et al., "Green tea polyphenol targets the mitochondria in tumor cells inducing caspase 3-dependent apoptosis", *Anticancer Research*, 23:1533-1540 (2003).

Hsu, et al., "Inhibition of autoantigen expression by (−)-epigallocatechin-3-gallate (the major constituent of green tea) in normal human cells", *J. Pharmacol Exp. Ther.*, 315(2):805-11 (2005).

Hsu, et al., "Green tea polyphenols induce differentiation and proliferation in epidermal keratinocytes", *J. Pharmacol. Exp. Ther.*, 306:29-34 (2003).

Hsu, et al., "Green tea polyphenols reduce autoimmune symptoms in a murine model for human Sjogren's syndrome and protect human salivary acinar cells from TNF-alpha-induced cytotoxicity", *Autoimmunity*. 40(21:138-47 (2007).

Hsu, et al., "Green tea polyphenol induces caspase 14 in epidermal keratinocytes via MAPK pathways and reduces psoriasiform lesions in the flaky skin mouse model", *Exp. Dermatol.*, 16(8):678-84 (2007).

Hsu, et al., "Use of avidin-biotin-peroxidase complex (ABC) in immunoperoxidase techniques: a comparison between ABC and unlabeled antibody (PAP) procedures", *J. Histochem. Cytochem.*, 29:577-580 (1981).

Hu, et al., "Caspase-14 is a novel developmentally regulated protease", *J. Biol. Chem.*, 273:29648-29653 (1998).

Katiyar, et al., "Green teapolyphenols: DNA photodamage and photoimmunology", *J. Photochem. Photobiol. B.*, 65(2-3):109-14 (2001).

Kazi, et al., "Potential molecular targets of tea polyphenols in human tumor cells: significance in cancer prevention", *In Vivo*, 16:397-403 (2002).

Kazi, et al., "Structure-activity relationships of synthetic analogs of (−)-epigallocatechin-3-gallate as proteasome inhibitors", *Anticanc. Res.*, 24(2B):943-954 (2004).

Kostovic and Pasic, "Phototherapy of psoriasis: review and update", *Acta Dermatovenerol Croat.*, 12(1):42-50 (2004).

Lambert, "Rationale and applications of lipids as prodrug carriers", *Eur. J. Pharm. Sci.*, 11 (Suppl 2):S15-27(2000).

Lazebnik, et al., "Nuclear events of apoptosis in vitro in cellfree mitotic extracts: a model system for analysis of the active phase of apoptosis", *J. Cell Biol.*, 123(1):7-22(1993).

Lippens, et al., "Caspase 14 is expressed in the epidermis, the choroid plexus, the retinal pigment epithelium and thymic Hassall's bodies", *Cell Death Differ.*, 10:257-9 (2003).

Lippens, et al., "Epidermal differentiation does not involve the pro-apoptotic executioner caspases, but is associated with caspase-14 induction and processing", *Cell Death Differ.*, 7:1218-1224 (2000).

Lippens, et al., "Vitamin D3 induces caspase-14 expression in psoriatic lesions and enhances caspase-14 processing in arganotypic skin cultures", *Am. J. Pathol.*, 165(3):833-41 (2004).

Madison, "Barrier function of the skin: "la raison d'etre" of the epidermis",*J. Invest. Dermatol.*, 121:231-41 (2003).

Marston, et al, "Effect of a complex environmental mixture from coal tar containing polycyclic aromatic hydrocarbons (PAH) on the tumor initiation, PAH-DNA binding and metabolic activation of carcinogenic PAH in mouse epidermis", *Carcinogenesis*, 22(7):1077-86 (2001).

*Martindale: The Complete Drug Reference, 32nd Ed.*, (Parfitt, ed.), pp. 367-389, Pharmaceutical Press: Chicago, IL (1999).

Medina, at al., "Assessment of the phototoxic potential of compounds and finished topical products using a human reconstructed epidermis", *In Vitr. Mol. Toxicol.*, 14(3):157-68 (2001).

Mizen and Burton, "The Use of Esters as Prodrugs for Oral Delivery of 0-Lactam antibiotics", *Pharm. Biotech.*, 11:345-365 (1998).

Morita, et al., "Cutaneous ultrastructural features of the flaky skin (fsn) mouse mutation", *J. Dermatol.*, 22(6):385-95 (2005).

Mukhtar and Ahmad, "Tea polyphenols: prevention of cancer and optimizing health", *Am. J. Clin. Nutr.*, 71(suppl):1698S-1702S (2000).

Nickoloff, et al., "Life and death signaling pathways contributing to skin cancer", *J. Investig. Dermatol. Symp. Proc.*, 7(1):27-35 (2002).

Oya and Schulz, "Decreased expression of p57(KIP2) mRNA in human bladder cancer", *Br. J. Cancer.*, 83(5):626-31 (2000).

Pauletti, et al., "Improvement of oral peptide bioavailability: Peptidomimetics and prodrug strategies", *Adv. Drug Deliv. Rev.*, 27(2-3):235-256 (1997).

Pistritto, et al., "Expression and transcriptional regulation of caspase-14 in simple and complex epithelia", *Cell Death. Differ.*, 9:995-1006 (2002).

Rendl, et al., "Caspase-14 expression by epidermal keratinocytes is regulated by retinoids in a differentiation-associated manner", *J. Invest. Dermatol.*, 119:1150-1155 (2002).

Rojas, et al., "Myeloperoxidase—463A variant reduces benzo[a]pyrene diol epoxide DNA adducts in skin of coal tar treated patients", *Carcinogenesis*, 22(7):1015-1018 (2001).

Rozen and Skaletsky, "Primer3 on the WWW for general users and for biologist programmers", *Methods Mol. Biol.*, 132:365-386 (2000).

Rubin, "Synergistic mechanisms in carcinogenesis by polycyclic aromatic hydrocarbons and by tobacco smoke: a bio-historical perspective with updates", *Carcinogenesis*, 22(12):1903-30 (2001).

Sadzuka, "Effective prodrug liposome and conversion to active metabolite", *Curr. Drug Metab.*, 1(1):31-48 (2000).

Sano, et al., "Stat3 links activated keratinocytes and immunocytes required for development of psoriasis in a novel transgenic mouse model", *Nat. Med.*, 11(1):43-49 (2005).

Schon, et al., "Pathogenic function of IL-1 beta in psoriasiform skin lesions of flaky skin (fsn/fsn) mice", *Clin. Exp. Immunol.*, 123(3):505-10 (2001).

Singh, et al., "Epigallocatechin-3-gallate selectively inhibits interleukin-I beta-induced activation of mitogen activated protein kinase subgroup cJun N-terminal kinase in human osteoarthritis chondrocytes", *J. Orthop. Res.*, 21(1): 102-9 (2003).

Stratton, et al., "The state-of-the-art in chemoprevention of skin cancer", *Eur. J. Cancer*, 36:1292-7, 2000.

Sundberg, et al., Full-thickness skin grafts from flaky skin mice to nude mice: maintenance of the psoriasiform phenotype', *J. Invest. Dermatol.*, 102(5):781-8 (1994).

Tedeschi, et al., "Green tea inhibits human inducible nitric-oxide synthase expression by down-regulating signal transducer and activator of transcriptionlalpha activation", *Mol. Pharmacol*, 65(1):111-20 (2004).

Thein, et al., "A strong genotoxic effect in mouse skin of a single painting of coal tar in hairless mice and in MutaMouse", *Muta Res.*, 468(2):117-124 (2000).

Van De Craen, et al., "Identification of a new caspase homologue: caspase-14", *Cell. Death Differ.*, 5:838-846 (1998).

Vayalil, et al., "Treatment of green tea polyphenols in hydrophilic cream prevents UVB-induced oxidation of lipids and proteins, depletion of antioxidant enzymes and phosphorylation of MAPK proteins in SKH-1 hairless mouse skin", *Carcinogenesis*, 24:927-36 (2003).

Vogel, et al., "Pharmacological coal tar induces G:C to T:A transversion mutations in the skin of MutaMouse", *Pharmacol Toxicol.*, 89(1):30-34 (2001).

Walsh, et al., "Psoriasis is characterized by altered epidermal expression of caspase-14, a novel regulator of keratinocyte terminal differentiation and barrier formation", *J. Dermal Sci.*, 37(1):61-3 (2005).

Wan, et al., "Structure-activity study of epi-gallocatechin gallate (EGCG) analogs as proteasome inhibitors", *Bioorg. Med. Chem.*, 13:2177-2185 (2005).

Wan, et al., "Study of the green tea polyphenols catechin-3-gallate (CG) and epicatechin-3-gallate (ECG) as proteasome inhibitors", *Bioorg. Med. Chem.*, 12(13):3521-7 (2004).

Wang, et al., "Prodrug approaches to the improved delivery of peptide drugs", *Curr. Pharm. Design.*, 5(4):265-287 (1999).

Wermuth, et al., "Designing Prodrugs and Bioprecursors I. Carrier Prodrugs", *Pract. Med. Chem.*, 671-696 (1996).

Wood and Earnshaw, "Mitotic chromatin condensation in vitro using somatic cell extracts and nuclei with variable levels of endogenous topoisomerase II", *J. Cell Biol.*, 111(6 Pt 2):2839-50 (1990).

Xia, et al., "Transgenic delivery of VEGF to mouse skin leads to an inflammatory condition resembling human psoriasis", *Blood*, 102(1):161-8 (2003).

Yamamoto, et al., "Green tea polyphenol causes differential oxidative environments in normal vs. malignant cells", *J. Pharmacol. Exp. Ther.*, 307(1):230-6 (2003).

Yamamoto, et al., "EGCG-targeted p57/KIP2 reduces tumorigenicity of oral carcinoma cells: role of c-Jun N-terminal kinase", *Toxicol. Appl. Pharmacol.*, 224(3):318-25 (2006).

Yang, et al., "Inhibition of carcinogenesis by tea", *Annu. Rev. Pharmacol. Toxicol.*, 42:25-54 (2002).

Yoneda, et al., "p53 gene mutations and p21 protein expression induced independently of p53, by TGF-beta and gamma-rays in squamous cell carcinoma cells", *Eur. J. Cancer*, 35:278-83 (1999).

Zenz, et al., "Psoriasis-like skin disease and arthritis caused by inducible epidermal deletion of Jun proteins", *Nature-*, 437(7057):369-75 (2005).

Zhoa, et al., "Apoptosis of mouse liver nuclei induced in the cytosol of carrot cells", *FEBS Lett.*, 448(1):197-200 (1999).

Zollner, et al., "Animal models of T-cell-mediated skin diseases", *Bioessays*, 26(6):693-6 (2004).

\* cited by examiner

MODIFIED GREEN TEA POLYPHENOL FORMULATIONS

CROSS-REFERENCE TO RELATED APPLICATION

This application is a filing under 35 U.S.C. §371 of PCT/US2006/031120 filed with the U.S. Receiving Office on Aug. 10, 2006, which claims the benefit of and priority to U.S. Provisional patent application No. 60/707,234 filed on Aug. 11, 2005, by Stephen D. Hsu, all of which are incorporated by reference in their entirety.

TECHNICAL FIELD

Aspects of the disclosure are generally related to green tea polyphenol compositions, more particularly, to lipid-soluble green tea polyphenol compositions.

BACKGROUND

More than 15 million people in the U.S. have symptoms of a skin disorder, for example dermatitis. Dermatitis is a term literally meaning "inflammation of the skin". It is usually used to refer to eczema, and several different forms are recognized including cercarial dermatitis, dermatitis herpetiformis, atopic dermatitis, seborrhoeic dermatitis, and contact dermatitis.

Cercarial dermatitis is a short-term, immune reaction occurring in the skin of humans that have been infected by water-borne trematode parasites. Symptoms, which include itchy, raised papules, commonly occur within hours of infection and do not generally last more than a week.

Dermatitis herpetiformis (DH) or Duhring's Disease, is a skin disorder often associated with celiac disease. It is a chronic, extremely itchy rash consisting of papules and vesicles. Dermatitis herpetiformis is associated with sensitivity of the intestine to gluten in the diet.

Atopic dermatitis, sometimes called eczema, is a kind of dermatitis, an atopic skin disease. Skin of an affected person reacts to irritants, food and air allergens and becomes red, flaky and very itchy. It also becomes vulnerable to inflammations caused by bacteria. Atopic dermatitis very often occurs together with other atopic diseases like hay fever, asthma and conjunctivitis.

Seborrheic dermatitis is a disease that causes flaking of the skin. It particularly affects the sebum-gland rich areas of skin. It can also affect the face and chest, and the creases of the arms, legs and groin. Seborrheic dermatitis usually causes the skin to look a little greasy and scaly or flaky. It is thought to be caused by a fungal infection caused by the yeast *Malassezia furfur* in individuals with decreased immunity and increased sebum production.

Domestic pets and animals also suffer from skin disorders including atopic dermatitis. Atopic dermatitis is one of the most common skin diseases of dogs. As with humans, the principal causes of atopic dermatitis are external allergens, e.g., house dust mites, pollens, molds, etc. Treatments include allergen avoidance and prevention of allergen contact, symptomatic anti-inflammatory pharmacotherapy, allergen-specific immunotherapy, and antimicrobial therapy.

Topical treatments for seborrheic dermatitis include shampoos containing coal tar, zinc pyrithione, salicylic acid or ketoconazole as active ingredients. Salicylic acid helps dissolve skin flakes. Pyrithione helps to kill fungus. Coal tar is believed to help reduce inflammation and sebum and to prevent the reoccurrence of flakes and scalp build-up. Coal tar is a combination of compounds produced from by-products of coal distillation, and a number of studies report that coal tar is toxic or carcinogenic. For example, coal tar contains benzo[a]pyrene, a highly potent carcinogen.

Studies have shown that topical application of compositions containing coal tar are toxic and may cause DNA damage (Thein, N. et al. (2000) Muta Res 468(2):117-24; Rojas, M. et al. (2001) Carcinogenesis 22(7):1015-8; Vogel, U. et al. (2001) Pharmacol Toxicol. 89(1):30-4).

Green tea polyphenols are known phytochemicals that have antioxidant, anti-microbial, anticancer, and anti-inflammation properties, and were recently found to promote skin homeostasis and protect against autoimmune diseases. Extracts of green tea have been used for medicinal purposes for generations in China. Green tea polyphenols in extracts are mostly water-soluble, and can be easily oxidized if they are mixed in emulsions containing water, such as detergents and cosmetics. Additionally, conventional green tea polyphenols are not permeable to the skin, and therefore their activity is significantly reduced.

Thus, there is a need for additional green tea polyphenol compositions and methods for preventing and treating skin disorders or symptoms thereof.

SUMMARY

Aspects of the disclosure generally provide modified green tea polyphenol compositions having one or more ester-linked $C_1$ to $C_{30}$ fatty acids or hydrocarbons. Cholesterol can also be linked to green tea polyphenols via an ether linkage. Green tea polyphenols that can be modified include, but are not limited to (−)-epicatechin (EC), (−)-epigallocatechin (EGC), (−)-epicatechin-3-gallate (ECF), (−)-epigallocatechin-3-gallate (ECGC), proanthocyanidins, enantiomers thereof, epimers thereof, isomers thereof, combinations thereof, and prodrugs thereof. The modified green tea polyphenols are more lipid-soluble than unmodified green tea polyphenols. It is believed that the increased lipid solubility increases the bioavailability of the green tea polyphenols and thereby increases the effectiveness of the green tea polyphenols. Green tea polyphenols are known to modulate gene expression and have been used in the treatment of cancer.

One aspect provides a compound according to Formula I:

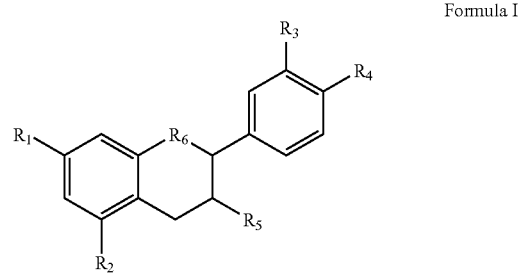

Formula I wherein $R_1$, $R_2$, $R_3$, $R_4$, $R_5$, are each independently H, OH,

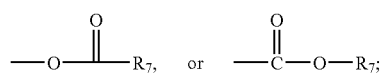

wherein $R_7$ is a linear, branched or cyclic, saturated or unsaturated, substituted or unsubstituted $C_1$-$C_{30}$ group, wherein if $R_7$ is cyclic, $R_7$ is a $C_3$-$C_{30}$ group; and $R_6$ is O, —$NR_8R_9$, or S, wherein $R_8$ and $R_9$ are independently hydrogen, or a linear, branched, or cyclic, saturated or unsaturated, substituted or unsubstituted $C_1$-$C_{30}$ group, wherein if $R_8$ and/or $R_9$ are cyclic, $R_8$ and/or $R_9$ are $C_3$-$C_{30}$ groups;

wherein at least one of $R_1$, $R_2$, $R_3$, $R_4$, $R_5$ is

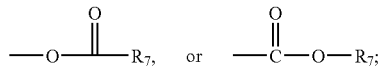

or a pharmaceutically acceptable salt or prodrug thereof.

Another aspect provides a compound according to Formula II:

Formula II

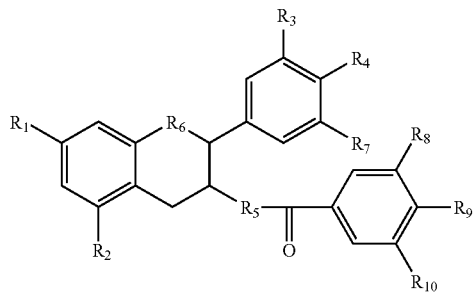

wherein $R_1$, $R_2$, $R_3$, $R_4$, $R_7$, $R_8$, $R_9$, and $R_{10}$ are each independently H, OH,

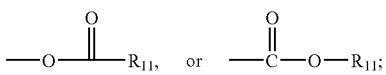

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups;

wherein $R_4$ is not

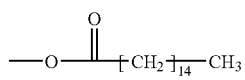

when $R_1$, $R_2$, $R_3$, $R_7$, $R_8$, $R_9$, and $R_{10}$ are OH;

wherein at least one of $R_1$, $R_2$, $R_3$, $R_4$, $R_7$, $R_8$, $R_9$, or $R_{10}$ is

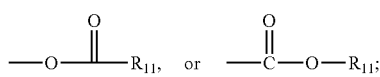

or a pharmaceutically acceptable salt or prodrug thereof.

Another aspect provides a compound according to Formula II:

Formula II

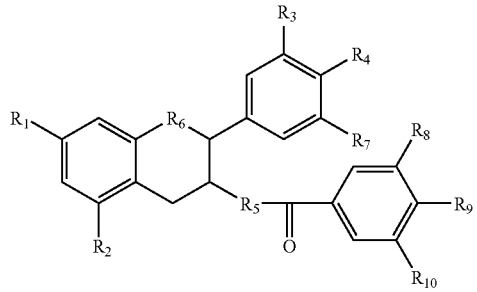

wherein $R_1$, $R_2$, $R_3$, $R_4$, $R_7$, $R_8$, $R_9$, and $R_{10}$ are each independently H, OH,

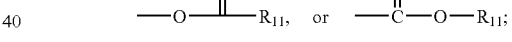

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups;

wherein at least two of $R_1$, $R_2$, $R_3$, $R_4$, $R_7$, $R_8$, $R_9$, or $R_{10}$ are —O—C(=O)—$R_{11}$, or —C(=O)—O—$R_{11}$;

or a pharmaceutically acceptable salt or prodrug thereof.

Compositions containing modified green tea polyphenols are provided as well as methods of using the compositions. In particular, compositions containing the disclosed modified green tea polyphenols in combination with a surfactant, detergent, oil, wax, or other hydrophobic vehicle are provided. One or more of the disclosed compounds and compositions can be used to treat skin disorders, for example dermatitis.

DETAILED DESCRIPTION

I. Definitions

Before explaining the various embodiments of the disclosure, it is to be understood that the invention is not limited in its application to the details of construction and the arrangement of the components set forth in the following description. Other embodiments can be practiced or carried out in various ways. Also, it is to be understood that the phraseology and terminology employed herein is for the purpose of description and should not be regarded as limiting.

Throughout this disclosure, various publications, patents and published patent specifications are referenced. Where permissible, the disclosures of these publications, patents and published patent specifications are hereby incorporated by reference in their entirety into the present disclosure to more fully describe the state of the art.

To facilitate understanding of the disclosure, the following definitions are provided:

As used herein, the singular forms "a," "an," and "the" include plural referents unless the context clearly dictates otherwise. Thus, for example, reference to "a factor" refers to one or mixtures of factors, and reference to "the method of treatment" includes reference to equivalent steps and methods known to those skilled in the art, and so forth.

"Acyloxy", as used herein, refers to a substituent having the following chemical formula:

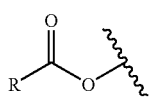

wherein R is a linear, branched, or cyclic alkyl, alkenyl, or alkynyl group.

"Alkoxy carbonyl", as used herein, refers to a substituent having the following chemical formula:

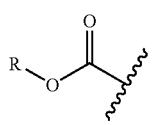

wherein R is a linear, branched, or cyclic alkyl group.

The term "alkenyl" refers to a monovalent, unbranched or branched hydrocarbon chain having one or more double bonds therein. The double bond of an alkenyl group can be unconjugated or conjugated to another unsaturated group.

The term "alkynyl" refers to a monovalent, unbranched or branched hydrocarbon chain having one or more triple bonds therein. The triple bond of an alkynyl group can be unconjugated or conjugated to another unsaturated group.

The term "cell" refers to a membrane-bound biological unit capable of replication or division.

The term "emulsion" refers to a mixture prepared from two mutually insoluble components. It is possible to generate mixtures of homogenous macroscopic appearance from these components through proper selection and manipulation of mixing conditions. The most common type of emulsions are those in which an aqueous component and a lipophilic component are employed and which in the art are frequently referred to as oil-in-water and water-in-oil emulsions. In oil-in-water emulsions the lipophilic phase is dispersed in the aqueous phase, while in water-in-oil emulsions the aqueous phase is dispersed in the lipophilic phase. Commonly known emulsion based formulations that are applied to the skin include cosmetic products such as creams, lotions, washes, cleansers, milks and the like as well as dermatological products comprising ingredients to treat skin conditions, diseases or abnormalities.

The term "Green Tea Polyphenols or GTP" refers to polyphenolic compounds present in the leaves of *Camellia sinensis*. Green tea polyphenols include, but are not limited to (–)-epicatechin (EC), (–)-epigallocatechin (EGC), (–)-epicatechin-3-gallate (ECF), (–)-epigallocatechin-3-gallate (ECGC), proanthocyanidins, enantiomers thereof, epimers thereof, isomers thereof, combinations thereof, and prodrugs thereof. Modified green tea polyphenols refers to a green tea polyphenol having one or more hydrocarbon chains, for example $C_1$ to $C_{30}$ and the compounds according to Formula I and II disclosed herein.

"Hydrophilic" as used herein refers to substances that have strongly polar groups that readily interact with water.

"Hydrophobic" as used herein refers to substances that lack an affinity for water; tending to repel and not absorb water as well as not dissolve in or mix with water.

The term "host" refers to a living organism, including but not limited to a mammal such as a primate, and in particular a human.

"Lipid soluble" as used herein refers to substances that have a solubility of greater than or equal to 5 g/100 ml in a hydrophobic liquid such as castor oil.

The term "lipid-soluble green tea polyphenol" refers to a green tea polyphenol having one more hydrocarbon chains having for example $C_1$ to $C_{30}$ groups linked to the polyphenol. $C_1$ to $C_{30}$ groups include for example cholesterol. Representative lipid-soluble green tea polyphenols include those according to Formula I and Formula II disclosed herein. The term is used interchangeably with "modified green tea polyphenol".

The term "pharmaceutically acceptable carrier" refers to a carrier or diluent that does not cause significant irritation to an organism and does not abrogate the biological activity and properties of the administered compound.

The term "pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the green tea polyphenols described herein, or a pharmaceutically acceptable salts thereof, with other chemical components, such as physiologically acceptable carriers and excipients. The purpose of a pharmaceutical composition is to facilitate administration of a compound to an organism.

The term "prodrug" refers to an agent, including nucleic acids and proteins, which is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11,: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curt. Pharm. Des., 5(4):265-87.

The term "substituted $C_1$ to $C_{30}$" refers to an alkyl, alkenyl, or alkynyl chain of one to thirty carbons wherein one or more carbons are independently substituted with one or more groups including, but not limited to, halogen, hydroxy group, aryl group, heterocyclic group, or alkyl ester. The range $C_1$ to $C_{30}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ etc. up to $C_{30}$ as wells as ranges falling within $C_1$ to $C_{30}$, for example, $C_1$ to $C_{29}$, $C_2$ to $C_{30}$, $C_3$ to $C_{25}$, etc. The range also includes less than $C_{30}$, less than $C_{19}$, etc.

The term "treating or treatment" refers to alleviating, reducing, or inhibiting one or more symptoms or physiological aspects of a disease, disorder, syndrome, or condition.

"Water soluble" as used herein refers to substances that have a solubility of greater than or equal to 5 g/100 ml water.

It will be appreciated that a numerical range provided herein includes each intervening integer

II. Modified Green Tea Polyphenol Compositions

Compositions containing green tea polyphenols modified to increase the permeability of the green tea polyphenols to skin and cell membranes or increase their solubility in hydrophobic media relative to unmodified green tea polyphenols are provided. Green tea polyphenols that can be modified include, but are not limited to (−)-epicatechin (EC), (−)-epigallocatechin (EGC), (−)-epicatechin-3-gallate (ECF), (−)-epigallocatechin-3-gallate (ECGC), proanthocyanidins, enantiomers thereof, epimers thereof, isomers thereof, combinations thereof, and prodrugs thereof. One embodiment provides a green tea polyphenol having an ester-linked $C_1$ to $C_{30}$ hydrocarbon chain, for example a fatty acid, at one or more positions. Another embodiment provides a green tea polyphenol having one or more cholesterol groups linked to the polyphenol. The cholesterol group can be linked for example by an ether linkage directly to the polyphenol or a $C_1$ to $C_{10}$ linker can connect the cholesterol group to the polyphenol.

Another embodiment provides a green tea polyphenol compound having one or more acyloxy groups, wherein the acyl group is $C_1$ to $C_{30}$. It is believed that the addition of alkyl, alkenyl, or alkynyl chains, for example via fatty acid esterification, to green tea polyphenols increases the stability of the green tea polyphenols and increases the solubility of the green tea polyphenols in hydrophobic media including lipids, fats, soaps, detergents, surfactants or oils compared to unmodified green tea polyphenols. Green tea polyphenols having one or more hydrocarbon chains, for example ester-linked $C_1$ to $C_{30}$ groups or $C_1$ to $C_{30}$ acyloxy groups are believed to more permeable to skin or cell membranes and thereby enable the ester-linked hydrocarbon chain containing or acyloxy containing green tea polyphenol to readily enter a cell and have a biological effect on the cell, for example modulating gene expression, compared to unmodified green tea polyphenols. It will be appreciated that one or more hydrocarbon chains can be linked to the green tea polyphenol using linkages other than ester linkages, for example thio-linkages. Esterified green tea polyphenols can be combined with oils, detergents, surfactants, or combinations thereof to produce compositions which clean the skin and deliver green tea polyphenols to the skin. The oils, detergents, or surfactants advantageously increase the stability of green tea polyphenols by reducing contact of the green tea polyphenols with aqueous media. Certain embodiments provide single optical isomers, enantiomers, or epimers of the disclosed modified green tea polyphenols. Other embodiments provide compositions containing single optical isomers, enantiomers, or epimers or the disclosed modified green tea polyphenols.

A. Modified Green Tea PolyPhenol

One embodiment provides a compound according to Formula I:

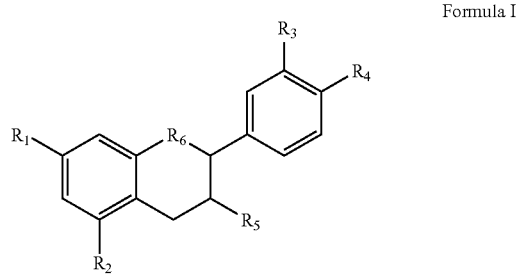

Formula I wherein $R_1$, $R_2$, $R_3$, $R_4$, and $R_5$, are each independently H, OH,

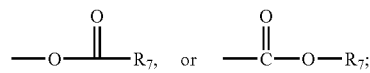

wherein $R_7$ is a linear, branched or cyclic, saturated or unsaturated, substituted or unsubstituted $C_1$-$C_{30}$ group, wherein if $R_7$ is cyclic, $R_7$ is a $C_3$-$C_{30}$ group; and $R_6$ is O, —$NR_8R_9$, or 5, wherein $R_8$ and $R_9$ are independently hydrogen, or a linear, branched, or cyclic, saturated or unsaturated, substituted or unsubstituted $C_1$-$C_{30}$ group, wherein if $R_8$ and/or $R_9$ are cyclic, $R_8$ and/or $R_9$ are $C_3$-$C_{30}$ groups;

wherein at least one of $R_1$, $R_2$, $R_3$, $R_4$, $R_7$, $R_8$, $R_9$, or $R_{10}$ is

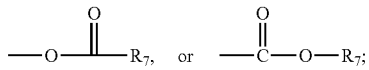

or a pharmaceutically acceptable salt or prodrug thereof, optionally in combination with an excipient.

One embodiment provides a compound according to formula I as described above wherein at least two of $R_1$, $R_2$, $R_3$, $R_4$, or $R_5$ are independently

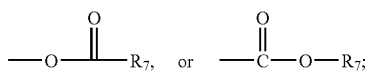

or a pharmaceutically acceptable salt or prodrug thereof, optionally in combination with an excipient.

Another embodiment provides a compound according to formula I as described above wherein at least three of $R_1$, $R_2$, $R_3$, $R_4$, or $R_5$ are independently

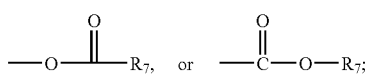

or a pharmaceutically acceptable salt or prodrug thereof, optionally in combination with an excipient.

Still another embodiment provides a compound according to formula I as described above wherein at least four of $R_1$, $R_2$, $R_3$, $R_4$, or $R_5$ are independently

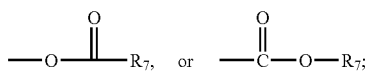

or a pharmaceutically acceptable salt or prodrug thereof, optionally in combination with an excipient.

Another embodiment provides a compound according to Formula II:

Formula II

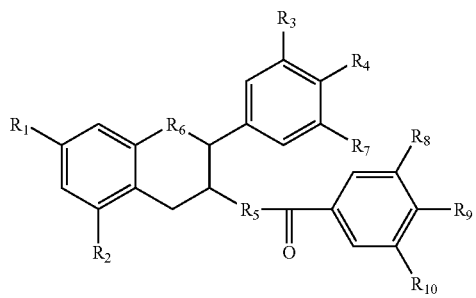

wherein $R_1$, $R_2$, $R_3$, $R_4$, $R_7$, $R_8$, $R_9$, and $R_{10}$ are each independently H, OH,

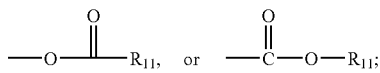

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups; and wherein at least one of $R_1$, $R_2$, $R_3$, $R_4$, $R_7$, $R_8$, $R_9$, and $R_{10}$ are independently

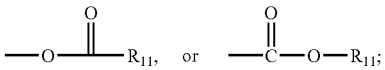

or a pharmaceutically acceptable salt or prodrug thereof, optionally in combination with an excipient.

Another embodiment provides a composition including a compound according to formula II wherein at least two of $R_1$, $R_2$, $R_3$, $R_4$, $R_7$, $R_8$, $R_9$, and $R_{10}$ are independently

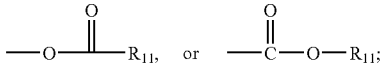

or a pharmaceutically acceptable salt or prodrug thereof, optionally in combination with an excipient.

Another embodiment provides a composition including a compound according to formula II as described above wherein at least three of $R_1$, $R_2$, $R_3$, $R_4$, $R_7$, $R_8$, $R_9$, and $R_{10}$ are independently

optionally in combination with an excipient.

Another embodiment provides a composition including a compound according to formula II as described above wherein at least four of $R_1$, $R_2$, $R_3$, $R_4$, $R_7$, $R_8$, $R_9$, and $R_{10}$ are independently

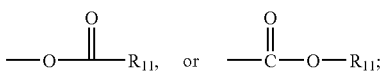

optionally in combination with an excipient.

Another embodiment provides a composition including a compound according to formula II wherein $R_1$, $R_2$, $R_3$, $R_4$, $R_7$, $R_8$, $R_9$, and $R_{10}$ are each independently H, OH,

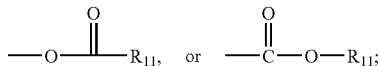

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups; and wherein at least one of $R_1$, $R_2$, $R_3$, $R_4$, $R_7$, $R_8$, $R_9$, and $R_{10}$ are independently

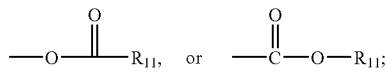

and wherein $R_4$ is not

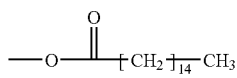

when $R_1$, $R_2$, $R_3$, $R_7$, $R_8$, $R_9$, and $R_{10}$ are OH;

or a pharmaceutically acceptable salt or prodrug thereof, optionally in combination with an excipient.

Another embodiment provides a green tea polyphenol esterified with at least two fatty acids. Representative green tea polyphenols include, but are not limited to (−)-epicatechin (EC), (−)-epigallocatechin (EGC), (−)-epicatechin-3-gallate (ECF), (−)-epigallocatechin-3-gallate (ECGC). Representative fatty acids include, but are not limited to butanoic acid, hexanoic acid, octanoic acid, decanoic acid, dodecanoic acid, tetradecanoic acid, hexadecanoic acid, 9-hexadecenoic acid, octadecanoic acid, 9-octadecenoic acid, 11-octadecenoic acid, 9,12-octadecadienoic acid, 9,12,15-octadecatrienoic acid, 6,9,12-octadecatrienoic acid, eicosanoic acid, 9-eicosenoic acid, 5,8,11,14-eicosatetraenoic acid, 5,8,11,14,17-eicosapentaenoic acid, docosanoic acid, 13-docosenoic acid, 4,7,10,13,16,19-docosahexaenoic acid, and tetracosanoic acid.

a. Excipients

Formulations including the lipid soluble green tea polyphenols according to Formula I, Formula II, or both may be prepared using pharmaceutically acceptable excipients composed of materials that are considered safe and effective and may be administered to an individual without causing undesirable biological side effects or unwanted interactions. The excipients are all components present in the pharmaceutical formulation other than the one or more lipid soluble green tea polyphenol compounds disclosed herein. As generally used herein "excipient" includes, but is not limited to, surfactants, emulsifiers, emulsion stabilizers, emollients, buffers, solvents and preservatives.

Preferred excipients include surfactants, especially nonionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

Emollients

Suitable emollients include those generally known in the art and listed in compendia, such as the "Handbook of Pharmaceutical Excipients", 4$^{th}$ Ed., Pharmaceutical Press, 2003. These include, without limitation, almond oil, castor oil, teratoma extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

Surfactants

Suitable surfactants include anionic surfactants, nonionic surfactants, cationic surfactants and ampholytic surfactants. Anionic surfactants include alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates. The alkyl or acyl group in these various compounds generally consists of a carbon-based chain containing from 8 to 30 carbon atoms.

Suitable anionic surfactants include fatty acid salts such as oleic, ricinoleic, palmitic and stearic acid salts; coconut oil acid or hydrogenated coconut oil acid; acyl lactylates, in which the acyl group contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

Suitable amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; ($C_8$-$C_{20}$)alkylbetaines, sulphobetaines, ($C_8$-$C_{20}$)alkyl-amido ($C_1$-$C_6$) or ($C_8$-$C_{20}$)alkyl-amido ($C_1$-$C_6$)alkylsulphobetaines. The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Disodium cocoamphodiacetate, disodium lauroamphodiacetate, disodium capryloamphodiacetate, disodium caproamphodiacetate, disodium cocoampho-dipropionate, disodium lauroamphodipropionate, disodium caproamphodipropionate, disodium capryloamphodipropionate, lauroamphodipropionate acid, and cocoamphodipropionate acid can also be used.

Representative cationic surfactants are chosen in particular from optionally polyoxyalkylenated primary, secondary or tertiary fatty amine salts; quaternary ammonium salts; imidazoline derivatives; or amine oxides of cationic nature.

Suitable quaternary ammonium salts are tetraalkylammonium halides (for example chlorides) such as, for example, dialkyldimethylammonium or alkyltrimethylammonium chlorides, in which the alkyl radical contains from about 12 to 22 carbon atoms, in particular behenyltrimethylammonium, distearyl-dimethylammonium, cetyltrimethylammonium or benzyl-dimethylstearylammonium chloride or alternatively the stearamidopropyldimethyl(myristyl acetate)ammonium chloride.

Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chlorides or methyl sulphate in particular) and mixtures thereof can also be used. The acyl groups preferably contain 14 to 18 carbon atoms and are more particularly obtained from a plant oil such as palm oil or sunflower oil.

Additional surfactants that can be used include, but are not limited to sodium dodecylsulfate (SDS), sodium cholate, sodium deoxycholate (DOC), N-lauroylsarcosine sodium salt, lauryldimethylamine-oxide (LDAO), cetyltrimethylammoniumbromide (CTAB), and bis(2-ethylhexyl)sulfosuccinate sodium salt.

Additional non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

Representative detergents include but are not limited to alkylbenzyldimethylammonium chloride, alkyldimethylbenzylammonium chloride, sodium bis(2-ethylhexyl)sulfosuccinate, bis(2-ethylhexyl)sulfosuccinate sodium salt, 3-[(3-Cholamidopropyl)dimethylammonio]-1-propanesulfonate.

Emulsifiers

Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Buffers

Buffers preferably buffer the composition from a pH of about 4 to a pH of about 7.5, more preferably from a pH of about 4 to a pH of about 7, and most preferably from a pH of about 5 to a pH of about 7.

The disclosed compositions can also contain at least one adjuvant chosen from the adjuvants usually used in cosmetics, such as fragrances, preserving agents, sequestering agents, wetting agents, sugars, amphoteric polymers, menthol, nicotinate derivatives, agents for preventing hair loss, foam stabilizers, propellants, dyes, vitamins or provitamins, acidifying or basifying agents or other well-known cosmetic adjuvants.

b. Bioactive Ingredients

Compositions containing the disclosed modified green tea polyphenols optionally include one more bioactive agents. In certain embodiments, one or more bioactive agents can be conjugated to the modified green tea polyphenol. Bioactive agents include therapeutic, prophylactic and diagnostic agents. These may be organic or inorganic molecules, proteins, peptides, sugars, polysaccharides, tea saponin, vitamins, cholesterol, or nucleic acid molecules. Representative vitamins include, but are not limited to lipid soluble vitamins such as vitamin D, vitamin E, or combinations thereof. Examples of therapeutic agents include proteins, such as hormones, antigens, and growth effector molecules; nucleic acids, such as antisense molecules; and small organic or inorganic molecules such as antimicrobials, antihistamines, immunomodulators, decongestants, neuroactive agents, anesthetics, and sedatives. Examples of diagnostic agents include radioactive isotopes and radiopaque agents.

Anti psoriasis Agents

In addition to the modified green tea polyphenols, suitable anti-psoriasis agents include without limitation salicylic acid; mometasone furoate; steroids including corticosteroids such as cortisone and oluxclobetasol propionate; 5-fluorouracil; epinephrine; anthralin; vitamin D3 analogs, such as calcipotriene; methotrexate; masprocol; trimethaxate gluconate; retinoids; cyclosporin; paclitaxel; 5-amino levulinic acid; bergasol; tin-ethyl etio purpurin; benzoporphyrin derivatives; antibodies, such as ABX-IL8 antibody, CD11a monoclonal antibody and ICM3 monoclonal antibody; enzyme inhibitors, including tryptase inhibitor and phospholipase A-2 inhibitors; angiogenesis blocking agents; T-cell blocking agents and mixtures thereof.

Anti-Fungal Agents

A variety of known antifungal agents can be used to prepare the described compositions. A list of potential antifungal agents can be found in "Martindale—The Complete Drug Reference", 32nd Ed., Kathleen Parfitt, (1999) on pages 367-389. Suitable antifungals include, without limitation, amphotericin, amorolfine, bifonazole, bromochlorosalicyanilide, buclosamide, butenafine, butoconazole, candicidin, chlordantoin, chlormidazole, chlorphenesin, chlorxylenol, ciclopirox olamine, cilofungin, clotrimazole, croconazole, eberconazole, econazole, enilconazole, fenticlor, fenticonazole, fluconazole, flucytosine, griseofulvin, hachimycin, haloprogin, hydroxystilbamine, isethionate, iodochlorohydroxyquinone, isoconazole, itraconazole, ketoconazole, lanoconazole, luflucarban, mepartricin, miconazole, naffifine, natamycin, neticonazole, nifuroxime, nystatin, omoconazole, oxiconazole, pentamycin, propionic acid, protiofate, pyrrolnitrin, ravuconazole, saperconazole, selenium sulfide, sertaconazole, sulbentine, sulconazole, terbinafine, terconazole, tioconazole, tolciclate, tolnaftate, triacetin, timidazole, undecenoic acid, voriconazole and combinations thereof. Some of these agents are known to have antibacterial activity as well.

In one embodiment, the anti-fungal agent(s) is an azole. Suitable imidazole and triazole antifungal agents are fluconazole, timidazole, secnidazole, miconazole nitrate, econazole, haloprogin, metronidazole, itraconazole, terconazole, posaconazole, ravuconazole, ketoconazole, clotimazole, sapirconazole and combinations thereof.

In an alternative embodiment, the anti-fungal agent(s) is chlorxylenol, undecyclenic acid, selenium sulfide, iodochlorohydroxyquinone, bromochlorosalicyanilide, triacetin or combinations thereof.

Other antifungal agents include bensuldazic acid, benzoic acid, biphenamine, cloconazole, cloxyquin, dermostatin, halethazole, monensin, oxiconazole, nitrate, pecilocin, pyrithione, rubijervine, terbinafine, ticonazole, and undecylinic acid.

Antibacterial Agents

A variety of known antibacterial agents can be used to prepare the described compositions. A list of potential antibacterial agents can be found in "Martindale—The Complete Drug Reference", 32nd Ed., Kathleen Parfitt, (1999) on pages 112-270. Classes of useful antibacterials include aminoglycosides, antimycobacterials, cephalosporins and beta-lactams, chloramphenicols, glycopeptides, lincosamides, macrolides, penicillins, quinolones, sulphonamides and diaminopyridines, tetracyclines, and miscellaneous. In a preferred embodiment, the antibacterial agent is selected from the group consisting of metronidazole, fimidazole, secnidazole, erythromycin, bactoban, mupirocin, neomycin, bacitracin, cicloprox, fluoriquinolones, ofloxacin, cephalexin, dicloxacillin, minocycline, rifampin, famciclovir, clindamycin, tetracycline and gentamycin.

Suitable aminoglycosides include antibiotics derived from *Streptomyces* and other actinomycetales, including streptomycin, framycetin, kanamycin, neomycin, paramomycin, and tobramycin, as well as gentamycin, sissomycin, netilmycin, isepamicin, and micronomycin.

Suitable antimycobacterials include rifamycin, rifaximin, rifampicin, rifabutinisoniazid, pyrazinamide, ethambutol, streptomycin, thiacetazone, aminosalicylic acid, capreomycin, cycloserine, dapsone, clofazimine, ethionamide, prothionamide, ofloxacin, and minocycline.

Cephalosporins and beta-lactams generally have activity against gram-positive bacteria and newer generations of compounds have activity against gram-negative bacteria as well. Suitable cephalosporins and beta-lactams include:

First generation; cephalothin, cephazolin, cephradine, cephaloridine, cefroxadine, cephydroxil, cefatrizine, cephalexin, pivcephalexin, cefaclor, and cefprozil.

Second generation; cephamandole, cefuroxime, cefonicid, ceforanide, cefotiam, and cephamycin.

Third generation; cefotaxime, cefmenoxime, cefodizime, ceftizoxime, ceftriaxone, cefixime, cefdinir, cefetamet, cefpodoxime, ceftibuten, latamoxef, ceftazidime, cefoperazone, cefpiramide, and cefsulodin.

Fourth generation: cefepime and cefpirome

Other cephalosporins include cefoxitim, cefmetazole, cefotetan, cefbuperazone, cefminox, imipenem, meropenem, aztreonam, carumonam, and loracarbef.

Chloramphenicols inhibit gram positive and gram negative bacteria. Suitable cloramphenicols include chloramphenicol, its sodium succinate derivative, thiamphenicol, and azidamfenicol.

Suitable glycopeptides include vancomycin, teicoplanin, and ramoplanin. Suitable lincosamides include lincomycin and clindamycin, which are used to treat primarily aerobic infections.

Macrolides have a lactam ring to which sugars are attached. Suitable macrolides include erytjhromycin, as well as spiromycin, oleandomycin, josamycin, kitamycin, midecamycin, rokitamycin, azithromycin, clarithromycin, dirithromycin, roxithromycin, flurithromycin, tylosin; and streptgramins (or synergistins) including pristinamycin, and virginiamycin; and combinations thereof.

Suitable penicillins include natural penicillin and the semisynthetic penicillins F, G, X, K, and V. Newer penicillins include phenethicillin, propicillin, methicilin, cloxacillin, dicloxacillin, flucloxacillin, oxacillin, nafcillin, ampicillin, amoxicillin, bacampicillin, hetacillin, metampicillin, pivampicillin, carbenecillin, carfecillin, carindacillin, sulbenecillin, ticarcillin, azlocillin, mezlocillin, piperacillin, temocillin, mecillinam, and pivemecillinam. Lactamase inhibitors such as clavulanic acid, sulbactam, and tazobacytam are often co-administered.

Suitable quinolones include nalidixic acid, oxolinic acid, cinoxacin, acrosoxacin, pipemedic acid, and the fluoroquinolones flumequine, ciprofloxacin, enoxacin, fleroxacin, grepafloxacin, levofloxacin, lomefloxacin, nadifloxacin, norfloxacin, ofloxacin, pefloxacin, rufloxacin, sparfloxacin, trovafloxacin, danofloxacin, enrofloxacin, and marbofloxacin.

Sulphonamides and diaminopyridines include the original of the "sulfa" drugs, sulphanilamide, and a large number of derivatives, including sulfapyridine, sulfadiazine, sulfafurazole, sulfamethoxazole, sulfadimethoxine, sulfadimethoxydiazine, sulfadoxine, sulfametopyrazine, silver sulfadiazine, mafenide acetate, and sulfasalizine, as well as related compounds including trimethoprim, baquiloprim, brodimoprim, ormetoprim, tetroxoprim, and in combinations with other drugs such as co-trimoxazole.

Tetracyclines are typically broad-spectrum and include the natural products chlortetracycline, oxytetracycline, tetracycline, demeclocycline, and semisynthetic methacycline, doxycycline, and minocycline.

Suitable antibacterial agents that do not fit into one of the categories above include spectinomycin, mupirocin, newmycin, fosfomycin, fusidic acid, polymixins, colistin, bacitracin, gramicidin, tyrothricin, clioquinol, chloroquinaldol, haloquinal, nitrofurantonin, nitroimidazoles (including metronizole, timidazole and secnidazole), and hexamine.

The antibiotic and antifungal agents may be present as the free acid or free base, a pharmaceutically acceptable salt, or as a labile conjugate with an ester or other readily hydrolysable group, which are suitable for complexing with the ion-exchange resin to produce the resinate.

Antiseptic Agents

Antiseptic agents can be included in compositions formulated for topical administration. Suitable antiseptic agents include iodine, iodophores including cadexomer iodine, chlorhexidine, gluconate, thimerosal, hydrogen peroxide, and peroxides and perchlorates including organic peroxides and perchlorate salts.

Skin Protectants

Skin protectants can be included in compositions formulated for topical administration. Such agents not only soothe the skin but may also aide in maintaining the integrity of the skin to prevent damage. Suitable skin protectants include allantoin; cocoa butter; dimethicone; kaolin; shark liver oil; petrolatum; lanolin; vegetable oils; ethoxylated oils and lipids; polymers such as polyalkylene oxides, polyvinylpyrrolidone, polyvinyl alcohol, poly(meth)acrylates, ethylvinyl acetate, polyalkylene glycols; polysaccharides and modified polysaccharides such as hyaluronic acid, cellulose ehers, cellulose esters, hydroxypropyl methylcellulose, crosscarmelose, and starch; natural gums and resins which may be gelling or non-gelling such as alginates, carrageenans, agars, pectins, glucomannans (guar, locust bean, etc.), galactomannans (e.g. konjac), gum arabic, gum traganth, xanthan, schleroglucan and shellac; and colloidal insolubles such as zinc oxide and other insoluble zinc salts, talcum powder and other micronized natural minerals; and colloidal silicas, aluminas and other metal oxides. Additional protectants include phenolic or non-phenolic phytochemicals including, but not limited to lycopene, beta-carotene, alpha-carotene, lutein, zeaxanthin, astaxanthin, non-carotenoid, erpeniods, perillyl alcohol, saponins, terpeneol, terpene limonoids, anthocyanins, catechins, isoflavones, hesperetin, naringin, rutin, quercetin, silymarin, tangeretin, tannins, phenolic acids, ellagic acid, chlorogenic acid, p-coumaric acid (para-coumeric acid), phytic acid, ferulic acid, vanillin, cinnamic acid, hydroxycinnamic acids, curcumin, resveratrol, lignans, glucosinolates, isothiocyanates, phenethyl, sothiocyanate, benzyl isothiocyanate, sulforaphane, indoles, indole-3-carbinol, thiosulfonates, phytosterols, beta-sitosterol, anthraquinones, senna, barbaloin, hypericin, capsaicin, piperine, chlorophyll, betaine and combinations thereof.

A wide variety of sunscreen actives are suitable. The exact amount and type of sunscreen that is used depends on the level of photoprotection that is desired. Generally any agent offering protection against ultraviolet radiation by absorbing, scattering or reflecting the ultraviolet radiation may be used herein. The sunscreen agents used herein may offer protection against one or more of the following forms of sunlight radiation UVA, UVB, UVC, visible light and infrared radiation. Generally the sunprotection factor (SPF) in the final formulation varies between 2 and 30, although products with SPFs up to 100 may be formulated. The sunscreen used herein may offer chemical or physical photoprotection.

Suitable sunscreen agents include those selected from the group comprising amino benzoic acid and derivatives, such as para-amino benzoic acid (PABA), glyceryl-PABA (Lisadimate), Padimate O, Roxadimate; anthrinalates, including methylanthrynilate; benzophenones, including dioxybenzone, oxybenzone and sulisobenzone, 3-benzophenone (Uvinul M40) 4-N,N-dimethylaminobenzoic acid ester with 2,4-dihydroxybenzophenone; camphor derivatives including 3-(4-methylbenzylidene)camphor, 3-benzylidene camphor; cinnamates including DEA-p-methoxycinnamate, ethylhexyl p-methoxy cinnamate, octocrylene, octyl methoxy cinnamate; dibenzoyl methanes including butylmethoxydibenzoylmethane, salicylates including, homomethyl salicylate, octyl salicylate, trolamine methyl salicylate; metal oxides including titanium dioxide, zinc oxide and iron oxide; 2-phenylbenzimidazole-5-sulfonic acid; 4,4-methoxy-t-butyldibenzoylmethane; and mixtures thereof.

Further non-limiting examples of sunscreens useful in accordance with the present invention are described in U.S. Pat. No. 5,087,445 to Haffey et al., U.S. Pat. No. 5,073,372 to Turner et al. and U.S. Pat. No. 5,160,731 to Sabatelli et al., all of which are incorporated herein by reference in their entirety.

Local Anesthetics or Antihistamines

Local anesthetics or antihistamines may also be employed in the topical formulation in order to lessen the pain and itching caused by the local infection. Suitable local anesthetics and antihistamines include benzocaine, lidocaine, dibucaine, etidocaine, benzyl alcohol, camphor, resorcinol, menthol, and diphenhdramine hydrochloride.

c. Veterinary Compositions

One embodiment includes the disclosed lipid soluble green tea polyphenols formulated for veterinary use, for example for domestic pets including domestic mammals such as dogs and cats. Topical veterinary formulations, for example shampoos, typically include weak detergents because animals have fewer layers of skin than humans. For example a cat's skin is 2-3 cell layers thick, while a dog's skin is 3-5 layers. Human skin, by contrast, is 10-15 cell layers thick.

Additionally, topical veterinary formulations optionally include a pesticide or insecticide to help control fleas, ticks, mites, mosquitoes, parasites, etc. Suitable pesticide or insecticide additives include natural or synthetic pyrethrins such as pyrethrin I and II, cinevin I and II, jasmolin I and II, allethrin, resmethrin, phenothrin, and permethrin or combinations thereof.

Organophosphates and organocarbamates can also be used with the disclosed compositions. Suitable organophosphates and organocarbamates include dichlorvos, cythioate, diazinon, malathion, carbaryl, fenthione, methylcarbamate, and prolate.

Additional insecticides include imidacloprid, fipronil, arnitraz, selamectin, nitenpyram, or combinations thereof.

Insect growth regulators and insect development inhibitors can also be used. Suitable insect growth regulators include methoprene, fenoxycarb, and pyriproxyfen. Suitable insect growth inhibitors include lufenuron and diflubenzuron.

d. Personal Care Products

Personal care products containing one or more of the modified green tea polyphenols can vary widely and include a skin care product, a hair care product, a beauty treatment product, a perfume, a bath and body product, a suncare product, a make-up and a toothpaste. These products may be prepared as formulations intended for specific use by individuals belonging to different age categories (babies, teenagers etc.), having different skin types (e.g. maturing, aged, dry, oily, mixed, combined or complexities thereof) or in accordance with the intended functionality of the product (for example products that prevent or reverse dehydration, replenish moisture, modulate pigmentation, prevent or reverse stretch marks, products for treatment or reversal of skin changes associated with aging such as wrinkles, blotches and atrophy or elastotic changes associated with intrinsic aging of the skin, as well as changes caused by external factors for example sunlight radiation, X-ray radiation, air pollution, wind, cold, dampness, dryness, heat, smoke and cigarette smoking).

Examples of skin care products which may be prepared using the disclosed compositions, for example emulsion formulations, include without limitation a skin cream; a facial cream; a cleanser, a toner; a day cream; a night cream; a day lotion; an eye cream; a facial mask (e.g. firming, moisturizing, purifying, deep-cleansing); an anti-aging cream; an anti-wrinkle cream; an anti-puffiness product; a cold weather cream; a foot cream; a facial scrub; an anti-acne product; a hand cream; an insect repellant formulation; or combinations thereof. The disclosed personal care products generally include an amount of one or more of the disclosed modified green tea polyphenols, for example a compound according to formula I or II, effective to reduce hyperproliferation of keratinocytes or reduce inflammation.

Suitable hair care products that may be prepared with the disclosed compositions include for example a shampoo; a conditioner; a re-conditioner; a mousse; a gel; a hair spray; a hair mascara; a hot oil treatment product; a dye; a hair mask; a deep conditioning treatment product; a coloring product; a hair-repair product and permanent wave product or combinations of thereof.

Representative beauty treatment products that can be produced using the disclosed compositions include without limitation, a waxing product, a pedicure product, a manicure product, a facial product, a beauty lift product, a massage product and an aroma-therapy product; and combinations thereof.

Bath and body products which may be prepared with the disclosed compositions include for example a shower gel; including an exfoliating shower gel; a foaming bath product (e.g., gel, soap or lotion); a milk bath; a body wash; a soap including liquid and bar soap; a cleanser, including a gel cleanser, a liquid cleanser and a cleansing bar; a body lotion; a body spray, mist or gel; an essential lotion; a slimming lotion; bath effervescent tablets; a hand and nail cream; a bath/shower gel; a shower cream; a cellulite smoothing product; a deodorant; a dusting powder; an antiperspirant; a depilatory cream; a shaving product e.g. a shaving cream, a gel, a foam and an after-shave, after-shave moisturizer; and combinations thereof.

Suncare products which may be prepared using the disclosed compositions include a sunscreen; a sunblocker; an after sun lotion milks and gel; a burn lotion; a tanning lotion, spray and milk; a sunless self-tanning cream, spray and lotion; a combined sunscreen-insect repellant formulation and combinations thereof.

Make-up or cosmetic products that may be prepared using the disclosed lipid-soluble green tea polyphenols include a mascara (thickening, lengthening, waterproof); a blush (cream and powder); a lipstick; a foundation cream (stick or liquid); a foundation powder, a concealer; an eye shadow (cream and powder); an eye pencil; an eye liquid line; a bronzing powder; a lip pencil; a lip gloss; a lip conditioner; a make-up remover (e.g. eye make-up remover); a liquid lip color; a brow pencil; a lip balm; a nail polish (base and top coat and nail blush); and a combination thereof.

e. Dermatological Products

Representative dermatological compositions containing one or more of the disclosed lipid-soluble green tea polyphenols include products which may be used to treat or reverse skin changes associated with aging such as wrinkles, blotches and atrophy or elastotic changes associated with intrinsic aging of the skin as well as changes caused by external factors for example sunlight radiation; X-ray radiation; air pollution; wind; cold; dampness; dryness; heat; smoke and cigarette smoking; external infectious agents such as fungi and bacteria; and combinations thereof. The disclosed compositions can be used to reduce hyperproliferation of keratinocytes.

Additional skin conditions which may be treated include products to treat infectious and non-infectious skin diseases. Infectious diseases include for example impetigo and leprosy. Non-infectious skin diseases include without limitation autoimmune disorders such as psoriasis, cutaneous systemic lupus, cutaneous rheumatoid arthritis, allergic skin disorders (e.g. eczema), and pemphigoid. It is believed that topical application of modified green tea polyphenols will protect the epidermis from symptoms associated with psoriasis by attenuating three keratinocyte-based mechanisms of pathogenesis: aberrant caspase 14 processing/nuclear localization, inflammation and hyperproliferation.

Various manifestations of eczema, psoriasis and acne may also be treated using the emulsions containing the disclosed modified green tea polyphenols. Clinical manifestations of eczema which may be treated include, inter glia, atopic eczema; allergic contact dermatitis; irritant contact dermatitis; infantile seborrhoeic eczema; adult seborrhoeic eczema; varicose eczema and discoid eczema. The manifestations of psoriasis that may be treated include chronic, plaque-type psoriasis; guttate psoriasis; psoriatic erythoderma; and pustular psoriasis. Acne conditions which may be treated include superficial acne (acne vulgaris), low grade acne, pre-acne and acne lesions including comedones and micro comedones.

Still further examples of dermatological products which may be formulated using the disclosed modified green tea polyphenols include without limitation products to treat hyper and hypopigmented skin, age spots, palmar or plantar hyperkeratosis, pruritis ichthyosis, Darier's disease, lichen simplex chronicus, hemorrhoids, inflammatory dermatosis, xeroderma pigmentosum, skin cancers including basal cell carcinoma, malignant cell carcinoma, squamous cell carcinoma, malignant melanoma, and AIDS-related Karposi sarcoma, premalignant skin lesions including actinic keratosis, xerosis, athletes foot, scabies, warts, herpes and dermatoses.

The particular product and the particular form in which the modified green tea polyphenols are present depend on how the product is applied. It is to be understood that the emulsion formulated with the modified green tea polyphenols may be applied in any product which is applied to the surface area of the human body.

III. Method of Making the Compositions a. Modified Green Tea Polyphenols

Modified green tea polyphenols having increased lipid solubility compared to unmodified green tea polyphenols can be produced for example, by the method described in Chen and Du, (2003) Chinese J Chem, 21:979-981, which where permissible is incorporated by reference in its entirety. Briefly, a green tea polyphenol is reacted with an acyl chloride having a desired number of carbons in ethyl acetate. The reaction is filtered and the reaction solution is washed with deionized water. The upper organic layer is evaporated and dried under vacuum. The lipid soluble green tea polyphenol can be isolated using high-speed counter-current chromatography as described for example in Chen et al. (2002) J. Chromatography, 982:163-165, which where permissible is incorporated by reference in its entirety. The isolated lipid soluble green tea polyphenol can then be formulated into a composition, for example topical formulations.

The water in oil topical compositions may be in the form of emulsions such as creams, lotions, ointments, powders, micro emulsions, liposomes, or in the form of gels, liquids, and foams. They may also be presented in dry powder formulations.

b. Emulsions

Generally emulsions are prepared in the presence of a multiplicity of other substances in order to achieve a desirable balance of emulsification, viscosity, stability and appearance. For example, the formulation of emulsions usually requires at least one, and frequently a combination of several, emulsifying agents. These agents facilitate the dispersal of one immiscible phase into the other and assist in stabilizing the emulsion. A comprehensive overview of emulsifying agents and their applications may be found in Becher, P. Encyclopedia of Emulsion Technology, Dekker Ed., 1983.

In one embodiment, the oil phase is prepared by mixing together one or more surfactant(s), optionally, one or more emulsifier(s), and one or more of the disclosed lipid soluble green tea polyphenols to melt if necessary. The aqueous phase is prepared separately by dissolving the preservatives in water with heating as needed. The aqueous phase is added to the oil phase, for example with continuous high shear mixing to produce a milky emulsion. The emulsion is cooled and the pH is adjusted by the addition of a buffer. The formulation is brought to the final weight by the addition of water.

The surfactants or detergents are optionally used in the compositions in proportions of between 0.01% and 50% by weight, relative to the total weight of the composition. When the compositions are in the form of shampoos, they are generally used in a proportion of at least 1% by weight, preferably between 5% and 50% by weight, relative to the total weight of the composition and in particular between 8% and 35%.

The concentration of the emulsifier(s) is from about 0.5% to about 50% by weight of the final composition. The concentration of the buffer(s) is from about 1% to about 25% by weight of the final composition and the concentration of the stabilizer(s) is from about 1% to about 25% by weight of the final composition.

The composition of the lipid soluble green tea polyphenol is about 0.01% to about 40% by weight of the final composition, in particular about 0.1%, 1.0%, 5%, 10%, 15%, 20%, 25%, 30%, or 35%. In certain embodiments one or more lipid soluble green tea polyphenols are present in an amount effective to reduce inflammation of the skin or treat dandruff when administered. The amount of the lipid soluble green tea polyphenol will vary according to skin disorder to be treated The concentration of an optional topical anesthetics is from about 1% to about 10% by weight and the concentration anti-fungals and other antibiotics is from about 0.3% to about 5% by weight. The concentration of insecticide can be from about 0.01% to about 10% by weight.

IV. Methods of Use

The disclosed compositions containing one or more lipid-modified green tea polyphenols are useful in topical application to the surface area of the human or animal body, including skin, hair, teeth, nails and lips. The compositions include personal care and dermatological products. Personal care products refer to all cosmetics, cosmeceuticals and beauty care products, all of which may be prepared in accordance with the present disclosure. Dermatological products refers to all products to treat or ameliorate skin conditions, abnormalities or diseases and contain one or more of the disclosed green tea polyphenols capable of improving said condition, abnormality, disease. These products include any and all products that may be used to treat or ameliorate any pathological conditions of the dermis or epidermis. It is noted that the modified green tea polyphenols may be applied in compositions which vary considerably in physical properties and use. The types and quantities of ingredients used to prepare different products will depend on the desired use of the product and may be varied in accordance with practices well known to those of ordinary skill in the art of formulating skin care and dermatological products.

One embodiment provides compositions including one or more of the disclosed modified green tea polyphenols, for example those according to Formulas I or II, for treating dermatitis. Such compositions are formulated for topical application to the skin as described above. The formulations can be applied directly to the skin in the form of lotions, creams, salves, ointments, fluids, hydrogels, foams, colloids, suspensions, or dry powder. In certain embodiments, the one or more of the disclosed modified green tea polyphenols, for example those according to Formulas I or II or both, are formulated in a shampoo or rinse for applying to the hair and scalp, for example a dandruff shampoo optionally including one or more anti-dandruff agents including but not limited to zinc pyrithione, salicylic acid or ketoconazole. The disclosed compositions can be used for treating dermatitis including dandruff. The disclosed modified green tea polyphenols can also be used in cosmetics, lip sticks, moisturizing lotions, and the like.

The disclosed modified green tea polyphenols can also be used for treating dermatitis in animals such as domestic mammals such as dogs and cats. Compositions including shampoos and lotions containing the compounds of Formula I, II or both can be applied to the skin of the animal and either rinsed off or allowed to be absorbed as needed. For example, the disclosed compositions can be applied to "hot spots" of a pet to help reduce inflammation, itching, and permit the skin to heal. The term "hot spots" refers to pyotraumatic dermatitis and are surface skin infections caused when populations of normal skin bacteria grow and overwhelm normal resistance.

EXAMPLE

Dandruff-Control Shampoo

A dandruff-control shampoo was formulated using green tea polyphenols esterified with mono unsaturated fatty acids (oleic acid, randomly esterified). A stock solution was prepared by dissolving lipid-soluble green tea polyphenols in 100% ethanol to produce a 60% w/v stock solution. The stock solution was mixed gently with commercially available standard shampoo as a vehicle at 1:20 and mixed until the ethanol evaporated. The standard shampoos contained the following ingredients: water (Aqua), ammonium lauryl sulfate, ammonium laureth sulfate, ammonium chloride, cocamide MEA, PEG 5 cocamide, fragrance (Parfum), hydroxypropyl methylcellulose, tetrasodium EDTA, DMDM hydantoin, citric acid, tocopheryl acetate (vitamin E acetate), methylchloroisothiazolinone, propylene glycol, honeysuckle extract (*Lonicera caprifolium*), methylisothiazolinone, aloe barbadensis gel (Aloe Vera), D&C green 5 (CI 61570), FD&C Yellow 5 (CI 19140). It will be appreciated that the vehicle can be any detergent, surfactant, oil, or emulsion.

The shampoo used as a vehicle was applied to patient for three months with no detectable reduction in dandruff. The vehicle shampoo was replaced with dandruff-control shampoo described above. The shampoo was used twice a day for for two days followed by once daily. The shampoo was applied to the hair, massaged into the scalp, and rinsed. In 24 h, visible changes occurred on the scalp with reduced flaking lesions and itchiness. After four days of treatment all lesions were cleared and no itchiness was reported.

I claim:
1. A composition comprising:
(a) one or more compounds according to Formula II:

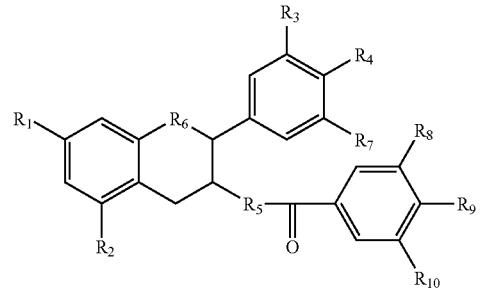

Formula II

Wherein $R_1$, $R_2$, $R_3$, $R_4$, $R_7$, $R_8$, $R_9$, and $R_{10}$ are each independently H, OH,

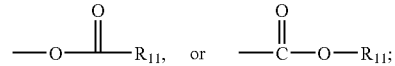

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ is O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups;

$R_6$ is independently O or S;

wherein at least one of $R_1$, $R_2$, $R_3$, $R_4$, $R_7$, $R_8$, $R_9$, or $R_{10}$ are independently

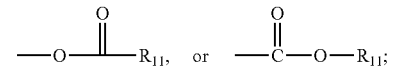

provided $R_4$ is not

when $R_1$, $R_2$, $R_3$, $R_7$, $R_8$, $R_9$, and $R_{10}$ are OH; or a pharmaceutically acceptable salt thereof; and (b) an excipient.

2. A composition according to claim 1, wherein one or more compounds according to Formula II are in an amount effective to reduce skin inflammation or dandruff.

3. The composition of claim 1 wherein at least two of $R_1$, $R_2$, $R_3$, $R_4$, $R_7$, $R_8$, $R_9$, and $R_{10}$ are independently

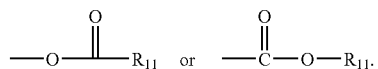

4. The composition of claim 1 wherein at least three of $R_1$, $R_2$, $R_3$, $R_4$, $R_7$, $R_8$, $R_9$, and $R_{10}$ are independently

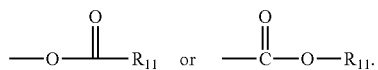

5. The composition of claim 1 wherein at least four of $R_1$, $R_2$, $R_3$, $R_4$, $R_7$, $R_8$, $R_9$, and $R_{10}$ are independently

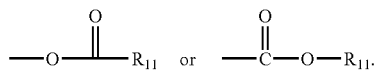

6. A compound according to formula II:

Formula II

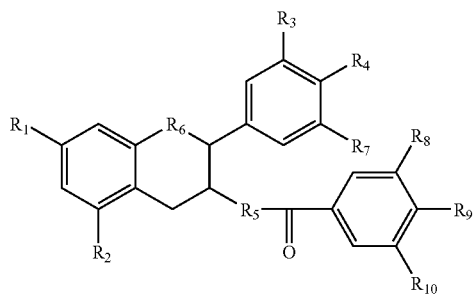

wherein $R_1$, $R_2$, $R_3$, $R_4$, $R_7$, $R_8$, $R_9$, and $R_{10}$ are each independently H, OH,

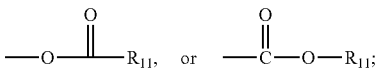

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ is O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups;

$R_6$ is independently O or S;

wherein at least one of $R_1$, $R_2$, $R_3$, $R_4$, $R_7$, $R_8$, $R_9$, or $R_{10}$ are independently

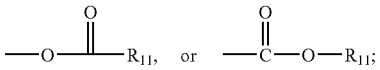

provided $R_4$ is not

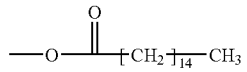

when $R_1$, $R_2$, $R_3$, $R_7$, $R_8$, $R_9$, and $R_{10}$ are OH;

or a pharmaceutically acceptable salt thereof.

7. A composition comprising the compound claim 6 in combination with an excipient.

8. An emulsion comprising one or more compounds according to claim 6.

* * * * *